United States Patent [19]
Mutsakis et al.

[11] Patent Number: 5,476,783
[45] Date of Patent: Dec. 19, 1995

[54] BIOREACTOR METHOD OF CULTURING AND PROPAGATING CELLS WITH A WOVEN MOTIONLESS MIXING ELEMENT

[75] Inventors: Michael Mutsakis, Brooklyn, N.Y.; Joseph P. Porcelli, Lyndhurst, N.J.

[73] Assignee: Koch Engineering Company, Inc., Wichita, Kans.

[21] Appl. No.: 114,462

[22] Filed: Aug. 31, 1993

Related U.S. Application Data

[63] Continuation of Ser. No. 855,532, Mar. 23, 1992, abandoned.

[51] Int. Cl.$^6$ .............................. C12N 5/00; C12M 3/04; C12M 1/14; C12M 1/02
[52] U.S. Cl. ................... 435/240.23; 435/289.1; 435/297.1
[58] Field of Search ..................... 435/240.1, 240.2, 435/240.23, 240.241, 284, 286, 310, 311, 313, 315, 316, 813; 210/615, 150, 151; 261/112.2, DIG. 72; 366/336–340

[56] References Cited

U.S. PATENT DOCUMENTS

| | | | |
|---|---|---|---|
| 3,785,620 | 1/1974 | Huber | 261/101 |
| 3,871,624 | 3/1975 | Huber et al. | 165/170 |
| 3,918,688 | 11/1975 | Huber et al. | 366/336 |
| 4,296,204 | 10/1981 | Grabner | 435/235 |
| 4,902,418 | 2/1990 | Ziegler | 422/143 |

FOREIGN PATENT DOCUMENTS

| | | | |
|---|---|---|---|
| 3028498 | 2/1988 | Japan | 435/288 |
| 0678632 | 10/1991 | Switzerland | 435/284 |
| 2178447 | 2/1987 | United Kingdom | 435/285 |

OTHER PUBLICATIONS

Paul, "Design and Scaleup of an Anchorage–Dependent Mammalian Cell Bioreactor", Annals New York Academy of Sciences, 589 (Biochem. Eng. 6), pp. 642–649, 1990.

*Primary Examiner*—William H. Beisner
*Attorney, Agent, or Firm*—Richard P. Crowley

[57] ABSTRACT

A bioreactor, motionless mixing element with attached cells, and method for the enhanced cultivation and propagation of cells in a bioreactor method, and which bioreactor comprises a housing and contains within the housing a motionless mixing element, the attachment of cells to the mixing element and a nutrient composition permitting the cell growth and division of the attached cells, and which motionless mixing element and the method and bioreactor comprise a porous, fibrous sheet material; for example, of a corrugated or knitted, woven wire material, such as stainless steel or titanium, and of selected dimensions as to the fiber diameter and height, to provide a maximum surface area for the attachment of the cells to be cultivated, with the ratio of the fibrous, geometric surface area of the porous, fibrous sheet material to that of a sheet material of the same shape being greater than about 1.0; for example, 1.5, and typically, for example, having a surface area for cell growth of about 2000 to 3000 $M^2/M^3$.

16 Claims, No Drawings

BIOREACTOR METHOD OF CULTURING AND PROPAGATING CELLS WITH A WOVEN MOTIONLESS MIXING ELEMENT

This is a continuation of application(s) Ser. No. 07/855,532 filed on Mar. 23, 1992, now abandoned.

BACKGROUND OF THE INVENTION

Bioreactors commonly have been employed for the cultivation and propagation of cells, such as mammalian cells, as well as the replication of virus-infected cells, in which the bioreactor comprises a housing in which nutrients are fed into the housing and the cells maintained under process conditions which permit cell growth and division within the housing, and, thereafter, the harvesting of the cells from the bioreactor.

It has been found that the use of a motionless mixing element, also known as a static mixing element, as a cell-culture propagator, is desirable, to enhance tissue-culture propagation within the bioreactor. For example, U.S. Pat. No. 4,296,204, issued Oct. 20, 1981, hereby incorporated by reference in its entirety, describes the advantages of employing certain motionless mixing elements in a housing, so that the surfaces of the motionless mixing element may be employed as a cell-growth surface by attachment of the cells, such as mammalian cells, to the surfaces of the motionless mixing element, typically by slow rotation of the elements within the housing. It is reported that the motionless mixing elements, such as a simple stationary baffle that utilizes the energy of the flowing fluids to produce mixing, result in consistent performance, regardless of flow rate and equipment dimensions. The employment of motionless mixing elements in bioreactors may be used to produce viral vaccines and to promote the growth and culture of mammalian cells. This U.S. patent describes particular motionless mixing elements comprised of an assembly of parallel sheets shaped to provide a plurality of channels, typically of corrugated form, which converge and diverge to form mixing cells.

The employment of motionless mixing elements in the design and scaleup of an anchorage-dependent, mammalian-cell bioreactor and in a method of cultivating also has been described recently in a publication *Annals New York Academy of Sciences*, "Design and Scaleup of an Anchorage-dependent Mammalian Cell Bioreactor", by Edward L. Paul, 589 (Biochem. Eng. 6), 642-9, 1990, hereby incorporated by reference in its entirety. This publication refers to the earlier cited U.S. Pat. No. 4,296,204 and sets forth test results achieved by employing Koch-Sulzer static mixing elements which are composed of titanium sheet material (Koch-Sulzer CY mixing elements), the sheets at a 45-degree angle and having a height of about ⅛th of an inch. It is stated that the test scaleup, employing the Koch-Sulzer motionless mixing sheet material, achieves uniform flow and distribution patterns over the cell surfaces, while operating at low fluid shear, and the Koch-Sulzer static mixing elements provide cell-attachment and growth surfaces for viral infection and replication in the cells.

The Koch-Sulzer static mixing elements, described in the 1990 publication, are described and claimed in U.S. patents in which motionless mixing packing elements are composed of sheets of corrugated lamellas, with the corrugations of adjacent lamellas oriented in different directions, while adjacent packing elements are angularly offset from each other. Typically the commercial embodiments, as tested and described in the publication, comprise sheet-metal materials (perforated or solid sheet metal) in a spaced-apart position, and which include a plurality of lamellas in contact with each other, and having corrugations therein, the corrugations sequentially arranged and oriented in different directions, the corrugations being disposed at an angle on a longitudinal axis, with the packing elements being angularly offset to an adjacent packing element, typically at about up to 90 degrees.

It is desirable to provide for a new and improved bioreactor containing motionless mixing elements, and to provide a method for the enhanced attachment and propagation of cells, in order to provide for enhanced production of the cultivated and propagated cells in the bioreactor.

SUMMARY OF THE INVENTION

The invention concerns a bioreactor containing a fibrous, motionless mixing element, to enhance the attachment of cells and cell growth within the bioreactor, and to a method of propagating cells and cell growth employing a bioreactor containing a fibrous, motionless mixing element.

It has been discovered that the employment of a motionless mixing element, composed of a porous, fibrous sheet material, rather than a solid or perforated sheet material as employed in the prior art, provides for significantly higher surface area per unit volume, so that significantly more cells can be attached to the surface of the motionless mixing element and be cultivated and propagated in the bioreactor.

The invention comprises a bioreactor consisting of a housing containing a motionless mixing element composed of a porous, open, fibrous sheet material, such as a corrugated or crimped sheet material with a plurality of sheets, with a motionless mixing element disposed within the bioreactor, and with the fibrous material of selected dimensions, to provide a maximum surface area for attachment of the cells in the bioreactor, the ratio of the fibrous, geometric surface area to that of a prior-art sheet or material of the same shape being greater than 1.0 for example, greater than about 1.5, thereby providing for enhanced cell propagation and enhanced cell attachment per unit volume.

Thus, in a method of the invention for the cultivation and propagation of cells, such as mammalian cells or virus-infected cells, the method comprises attaching the cells to the surface of a motionless mixing element disposed within a housing of a bioreactor, and maintaining the cells within the bioreactor in a condition of growth and propagation, and subsequently harvesting the cells, the improvement which comprises employing, as the motionless mixing elements within the bioreactor, a porous, fibrous sheet material of selected dimensions, to provide maximum surface area for the attachment of the cells. The geometric surface area of a motionless mixing element made of wire, such as a gauze; that is, the wire surface area, can be selected to be larger significantly than that of solid sheet metals previously employed in the prior art as the motionless mixing element. The higher the surface area per unit volume the more cells in the bioreactor that can attach and grow.

It is desirable to employ particular and selected fibrous; for example, wire, motionless mixing elements within a bioreactor for enhanced cell growth, to enhance surface area for cell attachment, typically, for cells of less than 10 microns in size; for example, mammalian cells. For example, wire gauze has been used to manufacture-commercial distillation packing, such as the Koch-Sulzer EX and BX structured packing. The surface area for such wire gauze-type distillation packing is based upon the surface area of a sheet. The sheet surface area is used in the Koch-Sulzer gauze packing publications and design calculations. The sheet surface area is used, because the small amount of liquid introduced into the gauze-type packing in distillation operations, which is the typical use, creates a liquid film, due to capillary action on the closely woven, wire gauze surface, and the exposed liquid surface area for mass transfer is, therefore, that of a sheet of liquid.

However, the geometric surface area of such wire gauze packing is much higher than the published sheet surface area. For example, the calculated ratios of the wire surface area to the geometric surface area, as of a sheet, for the various metal gauzes employed as the Koch-Sulzer motionless mixing elements, are as follows: For standard BX and CY metal gauze elements—1.68; for BX gauze type 83—1.53; and for EX gauze type—1.59. The term B designates about a ¼th-inch (6-millimeter) corrugation crimp height, C designates about a ⅛th-inch (3-millimeter) crimp height, Y designates a corrugation angle of 45 degrees, and X designates a corrugation angle of 30 degrees. It should be noted that the relative surface-area ratio is specific for the type of fiber or gauze employed and is independent of the geometry of the motionless mixing elements. In the attachment of cells to a motionless mixing element surface, to enhance cultivation and propagation of the cells, it is desirable, in the bioreactor and cell-propagation method, to achieve the higher surface area per unit volume. The higher the surface area per unit volume, the greater the number of cells that can be attached to the motionless mixing element surface.

As illustrated, based on the foregoing calculations, it is apparent that the maximum geometric surface area depends on gauze mesh size, as well as wire size, and those titanium gauze samples, having 1.225 and 2.141, as well as marginally 1.036, would be the selected gauze samples for use as a motionless mixing element in a bioreactor.

U.S. Pat. No. 3,785,620, describing metal-weave SMV packing for cocurrent (mixing) and countercurrent (distillation) applications, is referred to in the above-noted U.S. Pat. No. 4,296,204; however, there is no suggestion of use or selection of particular geometric surface areas in a bioreactor. U.S. Pat. No. 3,785,620 describes commercial motionless mixing elements, where a small quantity of liquid is introduced on top of the packing, and the small spaces between the wire gauze cause capillary action of the liquid. This allows the small quantity of liquid to wet the gauze packing in countercurrent distillation operations, which maximizes liquid surface area for mass transfer. The spaces between the wire gauze and the wire, itself, become coated with a continuous sheet of liquid. To contrast the operation of the gauze packing, if the same quantity of liquid was poured on top of an identical design made of sheet metal, the liquid would flow straight down the sheet and not spread out, because capillary action is not present in a prior used sheet-metal design.

The porous, fibrous sheet material, suitable for use in the motionless mixing elements of the invention, are those fibrous sheet materials which are porous, such as metal wire in tightly or closely woven gauze or knitted in corrugated form, which are sufficient to retain or approach plug flow required for motionless mixing, and to be characterized by good radial mixing properties. The fibers, such as the wire of a woven gauze sheet material, should be selected of sufficient dimensions and weave, to provide for a maximum, exposed, geometric surface area, to provide a maximum surface for the attachment of the cells. Generally, in the selection of a fiber size, the minimum fiber or wire size should be approximately 3,000ths of an inch, so as to provide a relatively flat surface area on the fiber surface for the attachment of the cells, which cells are typically less than 10 microns; for example, about 1 micron.

The porous fibrous sheet material typically has a geometric surface area for the cell propagation attachment of about $425 M^2/M^3$ or more.

The porous, fibrous sheet material employed as the motionless mixing element may comprise a woven or nonwoven material, and may be placed in a woven-weave form or a knitted form, and typically composed of corrugated sheets, and with a plurality of sheets disposed at an angle to each other, and generally of a corrugation height not greater than ½ inch (12.7 mm), typically ¹⁄₁₆th to ¼th of an inch (1.6 to 6.4 mm), to provide maximum surface area per unit volume. The fibers may be composed of any type of material which permits the attachment and acceptance of the cells to be cultivated and propagated, and may, for example, be composed of plastic fibers, such as nylon or other inert-type polymeric materials, such as porous, nonwoven fibrous sheets, or metal fibers, such as titanium, stainless steel, hastalloy, or coated metal fibers, such as stainless-steel titanium-coated metal fibers, or other metal fibers or wires coated with an inert metal, such as titanium, or glass fibers, such as borosilicate glass fibers, which may be in woven or nonwoven form. In one preferred embodiment, the porous, fibrous sheet material would comprise a woven or knitted, metal-wire, porous-type, corrugated sheet material composed of titanium or titanium-coated wires.

The method and the bioreactor of the invention may be employed in a variety of cell-propagation methods and techniques, such as those described and illustrated, for example, in the 1990 publication, by substituting the sheet-metal-type motionless mixing element for a porous, fibrous sheet material of selected dimensions, so that the geometric surface area would exceed that of the sheet material. It is recognized that not all wire-gauze-type sheet materials may be suitably employed, but only those selected to have a greater geometric surface area; otherwise, there would be no significant advantage over employing the porous, fibrous sheet material in a motionless mixing element over the typical sheet materials, such as the SMV motionless mixing elements described in U.S. Pat. Nos. 3,871,624 and 3,918,688, as suitable for use in cell propagation, and which patents describe motionless mixing elements made of offset, stacked, corrugated sheet metal.

The invention will be described for the purposes of illustration only, in connection with the illustrated embodiments; however, it is recognized that those persons skilled in the art may make various modifications, changes, additions and improvements to the illustrated embodiments, without departing from the spirit and scope of the invention.

DESCRIPTION OF THE EMBODIMENTS

It has been found surprisingly that, if the SMV mixing element, as used in the publication, supra, is manufactured from wire gauze, instead of sheet metal, the metal surface area for attachment and growth of small mammalian cells (less than 10 microns in size) is much larger than an SMV mixing element made of sheet metal in many instances. For example, the below-noted table, with examples of different, commercial, wire-gauze sizes, shows the calculated geometric surface area of a gauze made of thin wire, as compared to that of sheet metal of the same dimensions:

| Gauze Mesh Size (Wires per inch) | Wire Size (inches) | Material | Calculated Wire Gauze Geometric Surface Area to that of Sheet Metal |
| --- | --- | --- | --- |
| 40 × 200 | 0.0055 | Titanium | 2.072 |
| 150 × 150 | 0.0026 | Stainless | 1.225 |
| 100 × 100 | 0.002 | Titanium | 0.628 |
| 50 × 50 | 0.004 | Titanium | 0.628 |
| 14 × 110 | 0.011 | Titanium | 2.141 |
| 30 × 30 | 0.011 | Titanium | 1.036 |
| 18 × 18 | 0.011 | Titanium | 0.621 |

As can be seen in the column to the right, for the above-noted, commercially available wire gauzes, the geometric surface area of a few of the wire gauzes is larger than that of a piece of sheet metal of the same size; that is, having a surface-area multiplier greater than 1. Thus, a titanium, metal-wire, gauze motionless mixing element, having a ratio greater than 1.0; for example, 2.0 or more, should be employed, to prepare the SMV motionless mixing element, and used in a bioreactor and in those cell-growth examples of the publication.

For example, the geometric surface area of a 1-inch-long by 1-inch-wide sheet of the above noted 40×200 wire gauze can be calculated as follows:

[(0.0055) × (3.14) × (1") × (40)]
Surface area of 0.0055"-diameter
wire × 3.14 (circle surface area) ×
1"-long strip of wire × 40 wires
+
[(0.0055) × (3.14) × (1") × (200)]
Surface area of 0.0055"-diameter
wire × 3.14 (circle surface area) ×
1"-long strip of wire × 200 wires
=
0.69 square inches + 3.454 square inches = 4.144 square inches.

For a piece of sheet metal which is 1-inch long by 1-inch wide, the surface area is calculated as follows:

[(1")×(1")]×2=2 square inches

Surface area of sheet is 1 inch multiplied by 1 inch multiplied by 2, because there are two sides to a sheet capable of cells to grow on.

The 40×200 wire-gauze surface area to sheet-metal surface-area multiple is therefore:

4.144 gauze surface area (above) =
2.000 sheet surface area (above) =
2.072 gauze surface-area multiplier compared to sheet metal.

This means that, if a Koch-Sulzer DY motionless mixing element (1/16" crimp height, 45-degree angle) made of sheet metal that typically contains 1,700M$^2$/M$^3$ of surface area is manufactured instead, using the 40×200 wire gauze mentioned above, with a 2.072 surface-area multiplier, the bioreactor user will realize a surface area for cell growth of greater than 3000; for example, 3,440M$^2$/M$^3$.

What is claimed is:

1. In a method for culturing and growing of cells, which method comprises:

a) providing a bioreactor containing therein at least one motionless mixing element, the element composed of adjacent sheets of solid or perforated corrugated lamellas, with corrugations of adjacent sheets oriented in different directions and angularly offset from each other to form a plurality of passageways to provide plug flow and radial mixing of components within the motionless mixing element and to provide a geometric solid surface area for the attachment of cells;

b) attaching cells to be cultivated and propagated to the surface area of the motionless mixing element disposed within the bioreactor, and c) applying nutrients to the bioreactor and maintaining the attached cells under conditions which permit cell growth and division, to provide for the propagation of the attached cells, and harvesting the cells, the improvement which comprises:

employing as said sheets of said motionless mixing element a woven, porous, fibrous sheet material providing a woven geometric surface area, the woven, porous, fibrous sheet material of selected dimensions, including fiber diameter height and gauze/weave thickness, to provide for the attachment of the cells to the woven geometric surface area of the said motionless mixing element including said woven, porous, fibrous sheet material, with the ratio of the woven geometric surface area to that of said geometric solid surface area of the same motionless mixing element composed of said sheets of solid or perforated corrugated lamellas being greater than 1.0, thereby providing for a greater surface area per unit volume of cells, and permitting enhancement in the amount of cells that are attached to the said motionless mixing element geometric surface area.

2. The method of claim 1 wherein the woven, porous, fibrous sheet material has a fiber diameter of greater than about 1/3000th of an inch in diameter.

3. The method of claim 1 wherein the woven, porous, fibrous sheet material comprises a crimped or knitted sheet material.

4. The method of claim 1 wherein the woven, porous, fibrous sheet material comprises a metal-wire sheet material.

5. The method of claim 1 wherein the woven, porous, fibrous sheet material is composed of fibers selected from the group consisting of: glass, polymer and metal.

6. The method of claim 1 wherein the cells to be propagated in the bioreactor are less than about 10 microns in size.

7. The method of claim 1 wherein the woven, porous, fibrous sheet material comprises a corrugated sheet material having corrugations with a height of about 1/16th to 1/2 inch.

8. The method of claim 1 wherein the woven, porous, fibrous sheet material has a geometric surface area per unit volume of cells of about 425M$^2$/M$^3$ or more.

9. The method of claim 1 wherein the said ratio is greater than about 1.5.

10. The method of claim 1 wherein the cells are cells for the production of viral vaccines.

11. The method of claim 12 wherein the cells are anchorage-dependent mammalian cells.

12. The method of claim 1 wherein the motionless mixing element has the lamellas angularly offset to adjacent lamellas up to an angle of 90 degrees.

13. The method of claim 1 wherein the woven, porous, fibrous sheet material comprises metal wire of stainless steel or titanium.

14. The method of claim 1 wherein the woven, porous, fibrous sheet material has a geometric surface area with a per unit volume of cells of more than 3,000M$^2$/M$^3$.

15. In a method for the culturing and growing of cells, which method comprises:

a) providing a bioreactor containing therein at least one motionless mixing element, the element composed of adjacent sheets of solid or perforated corrugated lamellas, with corrugations of adjacent sheets oriented in different directions and angularly offset from each other to form a plurality of passageways to provide plug flow and radial mixing of at least two components within the motionless mixing element and to provide a solid geometric surface area for the attachment of cells;

b) attaching cells to be cultivated and propagated to the surface area of the motionless mixing element disposed within the bioreactor;

c) applying nutrients to the bioreactor and maintaining the attached cells under conditions which permit cell growth and division, to provide for the propagation of the attached cells, and harvesting the cells, the improvement which comprises:

employing as said sheets of said motionless mixing element a woven, porous, fibrous sheet material providing a woven geometric surface area, the woven, porous, fibrous sheet material of selected dimensions, including fiber diameter and gauze/weave thickness, to provide for the attachment of the cells to the woven geometric surface area of the said motionless mixing element including said woven, porous, fibrous sheet material, with the ratio of the woven geometric surface area to that of said solid geometric surface area of the same motionless mixing element composed of said sheets of solid or perforated corrugated lamella being greater than 1.5, thereby providing for a greater surface area per unit volume of cells, and permitting enhancement in the amount of cells that are attached to the said motionless mixing element geometric surface area;

d) the woven, porous, fibrous sheet material comprising a corrugated woven metal wire sheet material having corrugations with a height of about 1/16th to 1/2 inch;

e) the motionless mixing element having the lamellas angularly offset to adjacent lamellas up to an angle of 90 degrees; and f) the cells to be propagated in the bioreactor being less than about 10 microns in size.

16. A bioreactor for the culturing and growing of anchorage-dependent cells therein, and which bioreactor comprises:

a) a housing;

b) a motionless mixing element within the housing composed of woven, porous, fibrous, wire metal sheet material having a geometric surface area, the woven, porous, fibrous, wire metal sheet material of selected dimensions, including fiber diameter and gauze/weave thickness, to provide attachment of the cells to the said geometric surface area of the said motionless mixing element including said woven, porous, fibrous, wire metal sheet material, with the ratio of the said geometric surface area to that of a surface area of the same motionless mixing element composed of a solid, or perforated, sheet material being greater than 1.5, and to provide for a woven geometric surface area with a per unit volume of cells greater than $425 M^2/M^3$ thereby providing for a greater surface area per unit volume of cells, and permitting enhancement in the amount of cells that are attached to the said geometric surface area, to provide a plurality of channels therein which converge and diverge to form a plurality of mixing cells, each cell formed and bound by the junction of two inlet channels which converge toward each other at about right angles on one plane, and two outlet channels which diverge from each other at about right angles on another plane, the planes being rotated generally with respect to each other;

c) cells attached to the motionless mixing element for propagation for the cells;

d) a nutrient composition to permit the cell growth and division of the attached cells; and e) means to harvest the cells from the bioreactor after propagation.

* * * * *

UNITED STATES PATENT AND TRADEMARK OFFICE
CERTIFICATE OF CORRECTION

PATENT NO. : 5,476,783
DATED : December 19, 1995
INVENTOR(S) : Michael Mutsakis and Joseph P. Porcelli It is certified that error appears in the above-indentified patent and that said Letters Patent is hereby corrected as shown below:

col. 6, line 21, after "diameter", please insert --,--.

col. 6, line 56, after "claim", please delete "12" and insert --1--.

col. 7, line 31, after "corrugated", please delete "lamella" and insert --lamellas--.

col. 8, line 13, after "provide", please insert --for the--.

Signed and Sealed this

Twenty-first Day of May, 1996

Attest:

BRUCE LEHMAN

*Attesting Officer*     *Commissioner of Patents and Trademarks*